United States Patent [19]

Angel et al.

[11] 4,068,169

[45] Jan. 10, 1978

[54] METHOD AND APPARATUS FOR DETERMINING HEMATOCRIT

[75] Inventors: Henry Robert Angel; Bernard Otto Bachenheimer, both of Fairfield, Conn.

[73] Assignee: Hycel, Inc., Houston, Tex.

[21] Appl. No.: 725,268

[22] Filed: Sept. 21, 1976

[51] Int. Cl.² ............................................. G01N 27/00
[52] U.S. Cl. ................................ 324/71 CP; 235/92 PC; 328/115
[58] Field of Search ............... 324/71 CP; 235/92 PC; 328/111, 115

[56] References Cited

U.S. PATENT DOCUMENTS

| | | | |
|---|---|---|---|
| 3,439,267 | 4/1969 | Coulter et al. | 324/71 |
| 3,812,425 | 5/1974 | Miller | 324/71 CP |
| 3,878,369 | 4/1975 | Gahwiler | 235/92 PC |
| 3,890,568 | 6/1975 | Coulter et al. | 324/71 CP |
| 3,921,066 | 11/1975 | Angel et al. | 324/71 CP |
| 3,973,189 | 8/1976 | Angel et al. | 324/71 CP |

Primary Examiner—Rudolph V. Rolinec
Assistant Examiner—Vincent J. Sunderdick
Attorney, Agent, or Firm—Robert P. Cogan; Timothy L. Burgess

[57] ABSTRACT

An apparatus and method are provided for measuring hematocrit. A diluted blood sample is passed through a well-known conductivity sensor providing a sensor pulse for each sensed blood cell. Each pulse has a peak amplitude corresponding to the size of a blood cell passing through the sensor. During a first time period initiated by passing of the sensor pulse above a threshold level, the sensor pulse is coupled to peak detecting means, and a signal indicative of the level of the peak is generated and stored. The value of each stored signal is added to an integrator for a fixed period of time. The value stored by the integrator is thus indicative of hematocrit level for a known sample volume.

14 Claims, 4 Drawing Figures

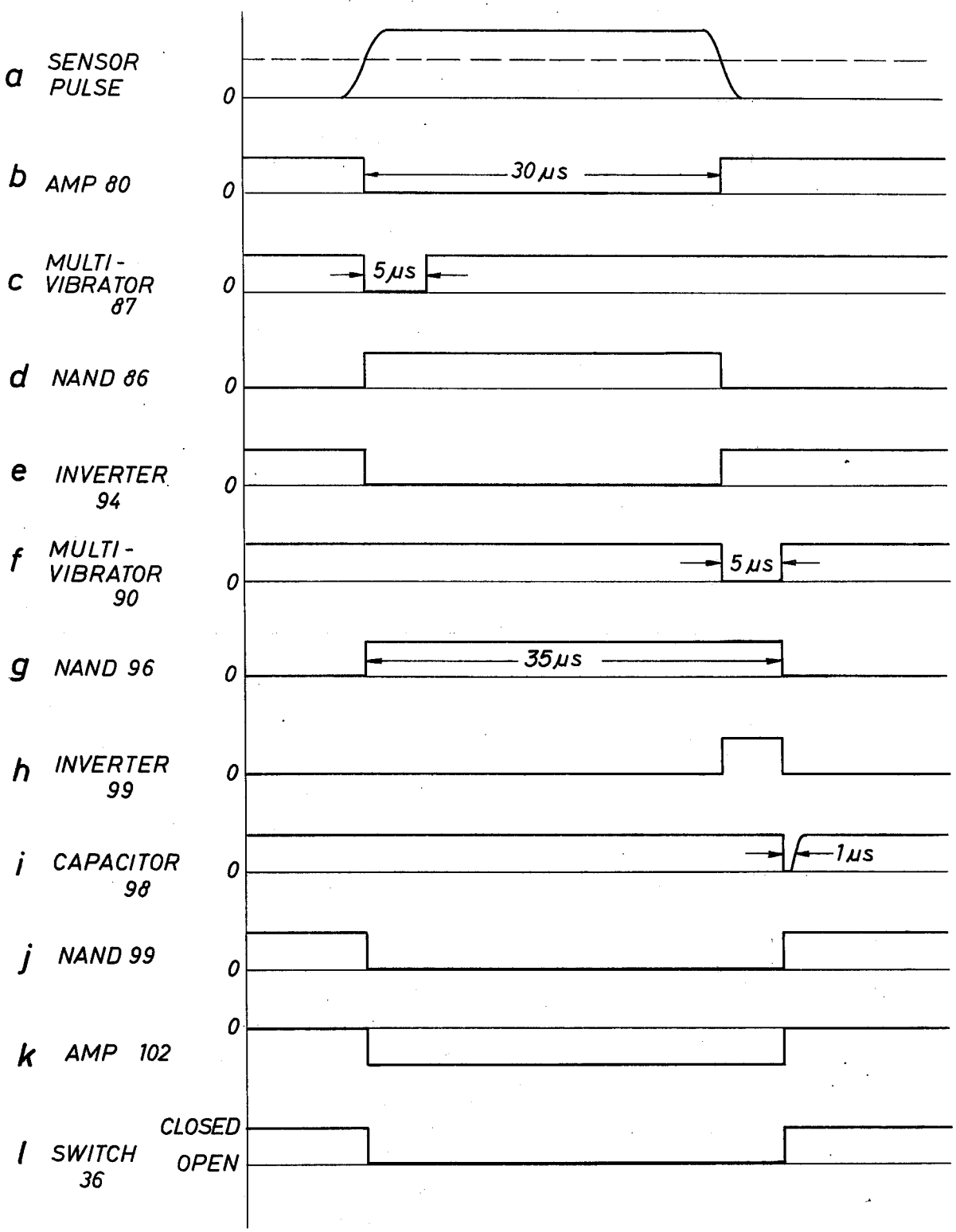

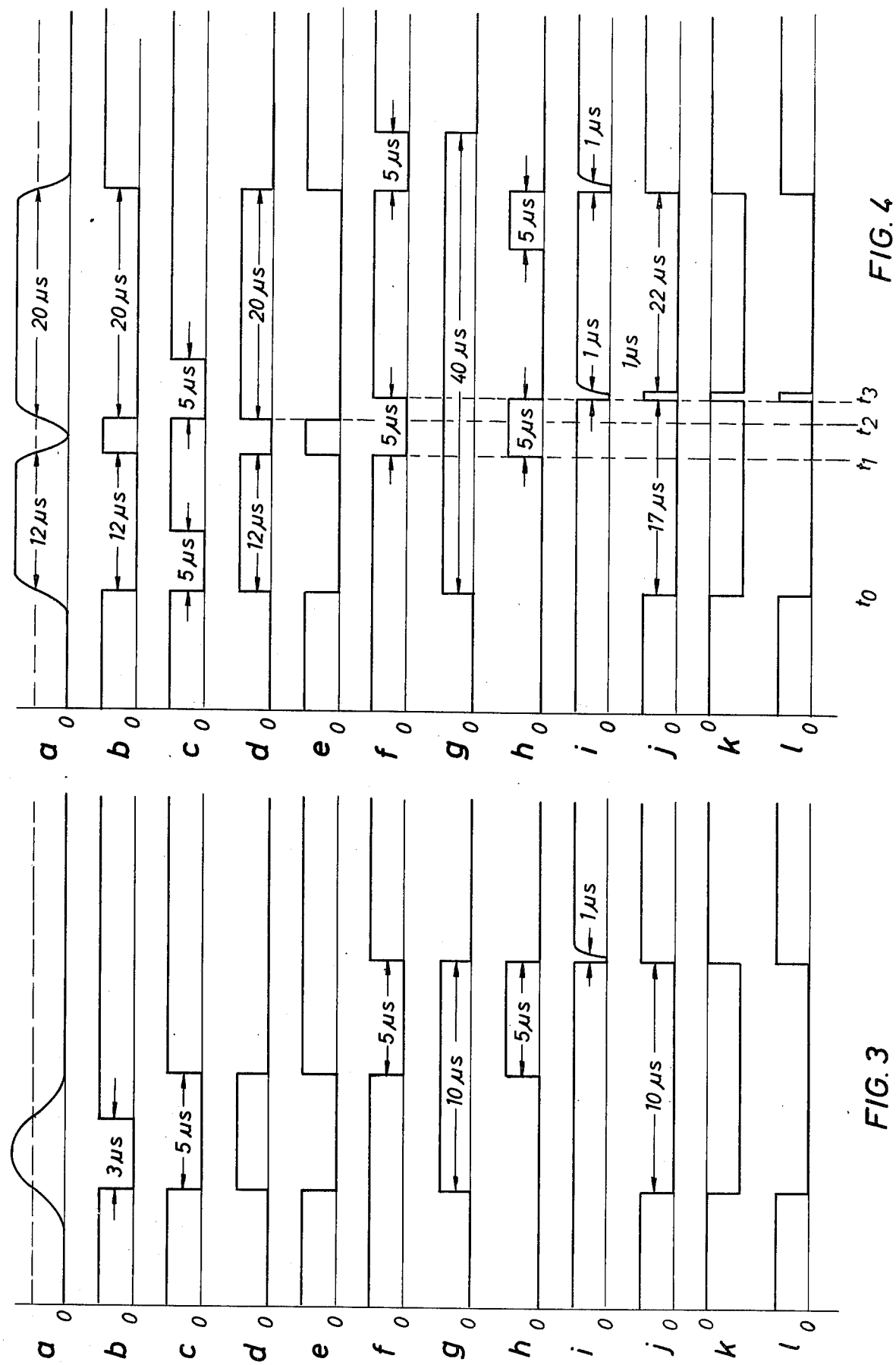

METHOD AND APPARATUS FOR DETERMINING HEMATOCRIT

BACKGROUND OF THE INVENTION

1. Field of Invention

The present invention relates to an apparatus and to a method for determining hematocrit.

2. Description of the Prior Art

Hematocrit is the percentage of packed red blood cells in a sample of whole blood. In the context contemplated for the present invention, hematocrit measurements are made in conjunction with a blood cell counter which includes a well-known conductivity sensor having an aperture and electrodes on either side thereof. A volume of a diluted blood sample is passed through the aperture, and conductivity changes due to blood cells passing through the aperture are monitored. Sensor pulses are produced representing the number of cells passing through the aperture, and each sensor pulse a peak representative of the volume of each cell (or group of cells resolved as a single cell). In earlier automatic hematology apparatus, a red blood cell count was provided in response to the number of pulses measured, and a calculation was made to determine means corpuscular volume (MCV). The hematocrit percentage was determined by multiplying the MCV times the red blood cell count and normalizing the results with respect to the volume passed through the sensor to obtain the hematocrit level as a percentage of the sample volume.

More recently, apparatus has been provided for direct determination of hematocrit. For example, U.S. Pat. No. 3,828,260 issued to Underwood on Aug. 6, 1974, discloses a hematocrit measuring apparatus in which a sensor pulse is stored and added to analog accumulation means for providing an analog level signal indicative of total cell volume of a sample. U.S. Pat. No. 3,812,425 issued to Miller on May 21, 1974, disclosed means for measuring hematocrit in which a sensor pulse peak is stored and in which the half-pulse level and threshold level of a trailing edge of the sensor pulse must be measured and processed to synchronize circuitry generating a pulse for addition to analog accumulation means which provide a level of analog voltage indicative of cell volume. Further, Miller's s apparatus must precisely time the accumulation, since volume measurements are not made. The Underwood apparatus, while providing satisfactory operation, utilizes the sensor pulse itself rather than intelligence generated therefrom for producing the hematocrit count. In the case of the Miller apparatus, many measurements must be made on each sensor pulse. Not all sensor pulses are substantially sinusoidal or bell-shaped. Depending on the orientation of a cell passing through the aperture or whether more than one cell is passing through the sensor at once, a sensor pulse may rise, fall, and rise again. Therefore, the number of direct measurements which must be made on the sensor pulse tends to decrease reliability of the hematocrit measuring means.

SUMMARY OF THE INVENTION

The present invention comprehends a method and apparatus for measuring hematocrit directly from sensor pulses. The invention is most conveniently utilized with a blood cell counter providing sensor pulses, sensor pulses being defined as described above. Such an apparatus is disclosed in U.S. Pat. No. 3,921,066 issued to Angel et al. on Nov. 18, 1975, now owned by the assignee herein, the disclosure of which is incorporated herein by reference. In the present apparatus, a first time period is established which is initiated by a presence of a sensor pulse exceeding a predetermined threshold level. During the first time period, the sensor pulse is monitored and the peak level thereof is detected. A value is generated and stored representing the peak level. In the preferred form, the first time period is equal to the period during which the sensor pulse exceeds the threshold level, with means being provided to determine a minimum span for the first time period. During a second time period, a value is added to accumulation means in accordance with the stored value, as by applying the stored signal to the accumulation means for a fixed time period. This procedure is repeated for each sensor pulse. The analog level in the accumulation means is indicative of volume of cells in a sample. The total value in the accumulation means may be related to the sample volume to provide an output in units of hematocrit percentage. In a further form, means are provided for responding to a next sensor pulse in the statistically less likely event of a next cell entering the aperture during processing of a first sensor pulse produced in response to a first cell passing through the sensor aperture.

It is thus an object of the present invention to provide improved hematocrit measuring apparatus in which a signal is generated and stored in response to measurement of the peak of a sensor pulse and in which accumulation means are incremented by an amount in correspondence with the level of the stored signal.

It is also an object of the present invention to provide means for directly measuring hematocrit in which a minimum number of measurements are made on a sensor pulse in order to generate intelligence indicative thereof and in which detection of a sensor pulse actuates timing means for incrementing accumulation means in correspondence with the magnitude of the sensor pulse.

It is a specific object of the present invention to provide a hematocrit measuring method and appratus in which an analog signal is generated indicative of the peak level of a sensor pulse and analog accumulation means are incremented for a preselected period of time at the level of the analog signal for each sensor pulse. It is a further object of the present invention, in one form, to provide in a means for measuring hematocrit of the type described, means for responding to a next sensor pulse occurring while a first sensor pulse is being measured.

BRIEF DESCRIPTION OF THE DRAWINGS

The means by which the foregoing objects and features of invention are achieved are pointed out with particularity in the claims forming the concluding portion of the specification. The invention, both as to its organization and manner of operation, may be further understood by reference to the following description taken in connection with the following drawings.

Of the drawings:

FIGS. 2, 3, and 4 are waveform charts useful in understanding the operation of the apparatus of FIG. 1.

DESCRIPTION OF THE PREFERRED EMBODIMENT

Figure 1:
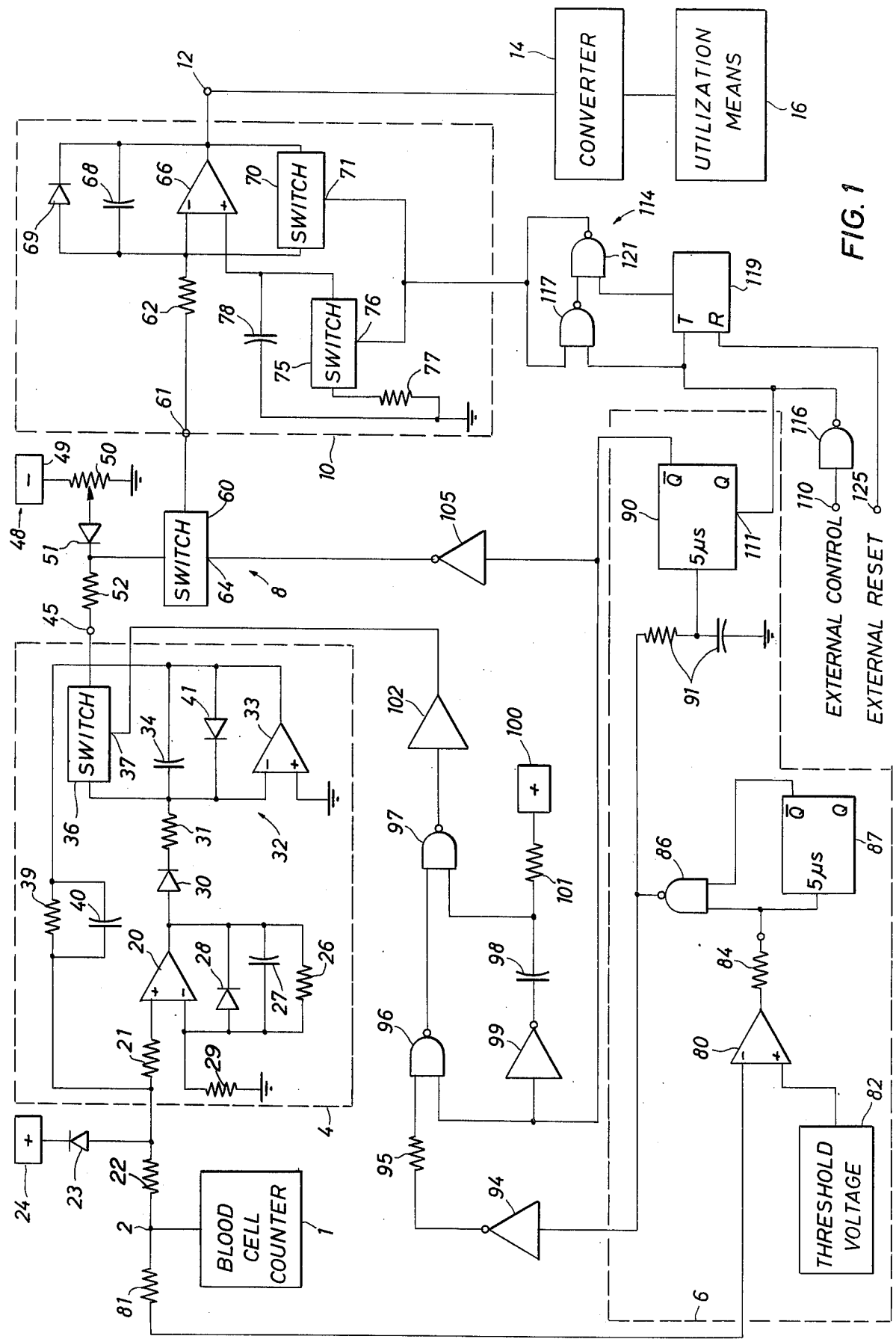
FIG. 1 is a schematic representation of hematocrit measuring apparatus constructed in accordance with the present invention.

Referring now to FIG. 1, there is illustrated in schematic form a hematocrit mesuring apparatus constructed in accordance with the present invention. Well-known blood cell measuring apparatus 1 provides sensor pulses to an input terminal 2. The measuring apparatus 1 preferably includes a conductivity sensor through which a diluted blood sample passes and a buffer amplifier at the output of which the sensor pulses are provided. In the preferred form, the blood cell measuring apparatus 1 comprises that which is disclosed in the above-cited patent to Angel et al. It is significant to note that the signal supplied to the input terminal 2 may be a non-corrected signal for coincidence of blood cells passing through the sensor in the measuring apparatus 1. The term blood cell (or cells) is used below to denote one or more blood cells resolved by the conductivity sensor as a single cell.

The sensor pulses are coupled from the terminal 2 to a peak detector and storage means 4 detecting the peak of the sensor pulse and for generating and storing a signal having a level indicative of the peak. Timing and control circuitry 6 is also coupled to the sensor pulse input terminal 2 for establishing a first time period during which the peak detector and storage means 4 is enabled to respond to a sensor pulse. This first time period is the longer of a minimum time span or the time during which a sensor pulse exceeds a threshold level. The peak detector and storage means 4 thus provides a stored signal indicative of the peak level of the sensor pulse. Consequently, the level of the stored signal is indicative of the volume of a cell passing through the sensor. Switching means 8 are provided coupled between the peak detector and storage means 4 and accumulation means 10 for providing an input indicative of the stored signal to the accumulation means 10. The timing and control means 6 also establishes a second time period during which the conductivity of the switching means 8 is controlled for the provision of a precise time integral of the level of the stored signal to the accumulation means 10. By applying the stored signal to the accumulation means 10 for a precise period of time, the accumulation means 10 is incremented by an amount indicative of the volume of a blood cell.

This process is performed for each sensor pulse produced in response to each cell in a sample passing through the sensor in the blood cell measuring apparatus 1. An analog output indicative of total blood cell volume is provided by the accumulation means 10 at a terminal 12. The terminal 12 may be connected to conversion means 14 which provides an output to display means 16. The conversion means 14 includes means for providing a scaling factor to relate the output at the terminal 12 to the total volume of the sample and the dilution ratio of the blood therein. This is done since it is desired to provide an output to the utilization means 16 indicative of hematocrit as a percentage of blood volume rather than an output in units of volume of blood cells. In the preferred embodiment, the blood cell measuring means 1 includes means for passing a sample of fixed volume through the sensor included therein. Therefore, the conversion means 14 may include scaling means in the form of a potentiometer. Further in the preferred embodiment, the conversion means 14 further comprises an analog to digital converter, and the utilization means 16 comprises a decoder, display driver, and digital display. Alternatively, the conversion means 14 may simply provide an analog output, and the utilization means 16 may simply comprise a meter.

Referring in greater detail to the circuitry of the preferred embodiment, the peak detector and storage means 4 comprises an operational amplifier 20 having its non-inverting input coupled by an input resistor 21 and a coupling resistor 22 to the input terminal 2. A diode 23 is connected between a terminal intermediate resistor 21 and 22 and a source of positive potential 24 for limiting the magnitude of input pulses applied to the operational amplifier 20 to a selected maximum determined by the level of positive potential. A conventional feedback loop consisting of a resistor 26, capacitor 27, and diode 28, all connected parallel, is connected from the output of the operational amplifier 20 to its inverting input, which also has a resistor 29 connected between the inverting input and a level of reference potential. In the present embodiment, the level of reference potential is ground. The diode 28 has its cathode connected to the output of the operational amplifier 20.

The amplifier 20 provides its output through a unilateral conducting means in the form of a diode 30 having its anode connected to the output of the operational amplifier 20 and its cathode coupled through a resistor 31 to an integrator 32 comprising signal generating and storage means. The integrator 32 includes an operational amplifier 33 having its inverting input connected to the terminal of the resistor 31 remote from the diode 30, its non-inverting input connected to ground, and a conventional feedback loop including a capacitor 34 connected between the output of the operational amplifier 33 and its inverting input. A controlled switching means comprising an analog switch 36 is connected across the capacitor 34. When the switch 36 is open, the peak detector and storage means 4 is enabled to respond to a sensor pulse. When the switch 36 is closed, the capacitor 34 is discharged, and the integrator 32 is reset. The switch 36 has a control terminal 37 connected to the timing and control means 6 for operation as described below. In order to provide for improved response, the integrator 32 is connected in a feedback loop of the input operational amplifier 20. The output terminal of the operational amplifier 33, which is also the output terminal of the integrator 32, is coupled by a feedback resistor 39 to the non-inverting input of the operational amplifier 20. A compensating capacitor 40 is connected across the feedback resistor 39. A diode 41 is connected across the capacitor 34 and poled to permit charging thereof only in the direction resulting from forward biasing of the diode 30.

When a sensor pulse appears at the input terminal 2, and the switch 36 is open, a signal is coupled through the diode 30 to the integrator 32. The absolute value of the output of the operational amplifier 20 continues to increase until the sensor pulse reaches a peak excursion. Upon decrease of the sensor pulse, the diode 30 becomes back biased. In this manner, the ingrator 32 generates a signal indicative of the peak level of an individual sensor pulse. This signal is stored by the integrator 32 and a potential having the level of the stored signal is provided at an output terminal 45 connected to the output of the operational amplifier 33. This potential level is maintained until the switch 36 is gated to reset the integrator 32. Thus an intelligence signal is generated in response to the sensor pulse indicative of the size of a cell in the sample.

Since there is a maximum potential level expected to be provided at the terminal 45 in response to a sensor pulse, limiting means 48 are connected to the terminal 50. A source of potential 49 is coupled by a potentiometer to a diode coupled by a resistor 52 to the terminal 45. The polarities of the diode 51 and source of potential 49 are selected to provide the limiting function in a well-known manner.

In order to control application of the potential level at the terminal 45 to the accumulation means 10, a controlled switching means in the form of an analog switch 60 is provided having a first terminal connected to the terminal of the resistor 52 remote from the terminal 45 and a second terminal connected to an input terminal 61 of the accumulation means 10. The analog switch 60 has a control terminal 64 operated by the timing and control means 6 as described further below. The accumulation means 10 comprises a conventional operational amplifier integrator including an operational amplifier 66 having its inverting input terminal coupled by an input resistor 62 to the input terminal 61. A feedback capacitor 68 is coupled from the output of the operational amplifier 66 to the inverting input thereof. A diode 69 is connected across the capacitor 68 poled for permitting charging only in the direction expected in response to a sensor pulse. An analog switch 70 comprising controlled switching means, is connected across the capacitor 68. The analog switch 70 has a control terminal 71 also coupled to the timing and control means 6.

The switch 70 is maintained open during a sampling period, during which a sample is passed through the sensor in the measuring apparatus 1 and also during a period of time thereafter in which it is desired to maintain the potential level generated at the output terminal 12. In order to minimize drift while holding the value generated at the terminal 12, compensating means are provided at the noninverting input terminal of the operational amplifier 66 rather than simply connecting the non-inverting input to ground. The compensating means comprises an analog switch 75 having a control terminal 76 and a resistor 77 connected in series between the non-inverting input of the operational amplifier 66 and ground. A capacitor 78 is connected across the analog switch 75 and resistor 77. Offset and other drift voltage generated within the operational amplifier 66 during a period in which the value at the output terminal 12 is held charge the capacitor 78 so that a compensating voltage is applied to the non-inverting input of the operational amplifier 66. The control terminal 76 is gated at the same time as the control terminal 71 when the sampling period and subsequent holding periods are ended.

The timing and control circuitry 6 includes an operational amplifier 80 having its inverting input coupled by a resistor 81 to the sensor pulse input terminal 2. The amplifier 80 comprises a threshold comparator. A source 82 of threshold potential is connected to the non-inverting input terminal of the operational amplifier 80. The output of the operational amplifier 80 is connected by a resistor 84 to a comparator output terminal 85. The level of potential supplied by the threshold potential source 82 is selected to determine the sensitivity of the threshold amplifier 80. The operational amplifier 80 is thus connected as a comparator. Potential levels of inputs to the operational amplifier 80 are selected such that a logic "one" is provided at the terminal 85 when no sensor pulse is present above the threshold level, and a logic "zero" is provided when a sensor pulse crosses the threshold level. The comparator output terminal 85 is connected to a first input of a NAND gate 86 and to the input of a one shot multivibrator 87 connected in a non-retriggerable mode having its output connected to another input of the NAND gate 86. The one shot multivibrator 87 is triggered on a negative-going transition; i.e., it is triggered in response to the presence of a sensor pulse exceeding the threshold level. The output o the NAND gate 86 will change state upon initiation of a sensor pulse and will remain in the changed state during the output period of the one shot multivibrator 87 and/or when a logic "zero" is at the comparator output terminal 85. Thus, means are provided for establishing a first time period equal to the duration of a sensor pulse above the threshold level, with a minimum time period established by the output provided by the one shot multivibrator 87. In the preferred embodiment, it is contemplated that the nominal sensor pulse will have a duration of 30 microseconds. The one shot multivibrator 87 is selected to provide an output having a duration of 5 microseconds.

A second one shot multivibrator 90 connected in a non-retriggerable mode is provided having its input terminal coupled to the output of the NAND gate 86 by an RC propogation compensating time constant circuit 91. The second one shot multivibrator 90 initiates a second time period at the end of the first time period. The timing signal provided from the one shot multivibrators 87 and 90 and NAND gate are utilized for maintaining the analog switch 36 in the integrator 32 open during the first and second time periods and otherwise closed. This is accomplished in the following manner.

The output of the NAND gae 86 is connected to an inverter 94 providing an output to a first input on a NAND gate 96 through an RC propogation compensating time constant circuit 95. The NAND gate 96 has a second input connected to the output of the one shot multivibrator 90. During a first time period initiated by a sensor pulse, the inverter 94 provides a logic "zero" and the one shot multivibrator 90 provides a logic "one". During the second time period the inverter 94 and one shot multivibrator 90 also provide outputs having opposite logic levels. At the termination of the second time perid both of these components provide logic "one" outputs. Thus the NAND gate 96 is utilized for providing a signal at a logic "one" for a time span equal to the sum of the first and second time periods.

The output of the NAND gate 96 is provided to a first input of a NAND gate 97. The NAND gate 97 has another second input coupled by a differentiating capacitor 98 to the output of an inverter 99. The input of the inverter 99 is connected to the output of the second one shot multivibrator 90 so that the inverter 99 provides a logic "one" only during a second time period and provides a transition to a logic "zero" at the end thereof. A source of potential 100 is coupled by a resistor 101 to provide a logic "one" to the second input of the NAND gate 97. However, a logic "zero" is AC coupled to the second input of the NAND gate 97 by the capacitor 98 at the end of a second time period. Thus means are provided for responding to the end of a second time period produced in response to a sensor pulse. The alternating current coupling of the inverter 99 to the NAND gate 97 is useful in providing for response to a next sensor pulse which may occur before the integrator 32 is discharged after having generated a signal in response to a first sensor pulse.

A buffer amplifier 102 is connected between the output of the NAND gate 97 and the gating terminal 37 of the analog switch 36. The analog switch 37 is held open during first and second time periods initiated in response to each sensor pulse, and is otherwise closed. The integrator 32 is maintained in a reset condition unless a sensor pulse is being measured. Spurious charging of the integrator 32 is prevented, and accuracy of the circuitry is maintained.

While the switch 36 is open, the integrator 32 generates and stores a signal indicative of the size of a cell indicated by a sensor pulse. The potential level of the signal is held at the terminal 45 until the integrator 32 is reset. This potential level is used to increment the accumulation means 10 by an amount indicative of the volume of the sensed cell represented by the sensor pulse in response to which the potential level is provided. Incrementing is done by closing the analog switch 60 for a fixed period of time for each signal provided at the terminal 45. In order to trigger the analog switch 60, the output terminal of the second one shot multivibrator 90 is connected to an inverter 105 having an output connected to the terminal 64 of the analog switch 60. After a first time period is completed and the peak detector and storage means 4 have provided a potential level at the output terminal 45, the analog switch 64 is gated during the second time period for a fixed time span to increment the accumulation means 10.

For enabling measurements during a sampling period during which measurements are made in response to a succession of sensor pulses, the timing and control means 6 further includes an enabling terminal 110 coupled to an enabling terminal 111 of the second one shot multivibrator 190 and to enabling circuitry 114 for the accumulation means 10. The enabling terminal 110 may be coupled and/or controlled by a red blood cell count function selection switch (not shown) in the measuring apparatus 1. The terminal 110 is also connected to an inverter 116 having output connected to a first input of an NAND gate 117 and is also connected to an enabling terminal of a clock circuit 119. The clock circuit 119 is a counter circuit used as a real time timer. The clock circuit 119 provides an output to a NAND gate 121 having its other input connected to the output of the NAND gate 117. The output of the NAND gate 121 is also connected to the gating terminal 71 and 76 of the respective analog switches 70 and 75 and to a second input of the NAND gate 117. The clock circuit 119 is also provided with an external reset terminal 125. The external reset terminal may be coupled to and/or controlled by a manual reset selection switch (not shown) in the measuring apparatus 1.

To enable counting, a logic "one" is applied to the terminal 110 and consequently, gating pulses are supplied at the terminals 76 and 71 to open the analog switches 75 and 70 respectively. The enabling pulse at the terminal 110 also initiates counting in the clock circuit 119. The clock circuit 119 has a preselected number preset therein so that when a preselected count is reached, the output supplied from the clock circuit 119 to the NAND gate 121 causes a change of state at the output thereof. The number in the clock circuit 119 may be, for example, selected such that the switches 70 and 75 may remain open for a maximum of 4 to 5 minutes. This allows for an expected sample measuring time of 30 seconds for measuring apparatus 1 and for holding the potential at the hematocrit analog output terminal 12 for 4 minutes. In a nominal embodiment, it is expected that the above described circuitry can maintain the potential level at the output terminal 12 within desired tolerances for that period of time. Alternatively, the NAND gates 117 or 121 may be supplied with inputs to gate the switches 70 and 75 to a closed state by either a logic "zero" applied to the enabling terminl 110 or by a reset pulse supplied to the external reset terminal 125 of the clock circuit 119.

OPERATION

Operation is further described with respect to FIGS. 2, 3, and 4 which are waveform charts illustrating the operation of the timing and control circuitry 6. The FIGS. 2, 3, and 4 each correspond to the operation in a different possible condition. FIG. 2 represents the normal case of operation in which a nominal sensor pulse is received. In the normal case, with sampling flow rates utilized, it is expected that a nominal sensor pulse will have a duration of approximately 30 microseconds (above the threshold level). In the preferred embodiment, the blood dilution utilized in the measuring apparatus 1 is 1:160,000. Consequently, in the normal case, it is not expected that a next sensor pulse will be produced while a first sensor pulse is being measured. FIG. 3 represents operation in the case in which a sensor pulse having a duration of less than 5 microseconds is produced. FIG. 4 is representative of the statistically less likely cae, but nonetheless occasionally expected, in which a next sensor pulse is produced while a first sensor pulse is being measured. In FIGS. 2, 3, and 4 all the representations have a common time abscissa, and the ordinates represent the state of the particular component referred to. FIG. 2 consists of FIGS. 2a through 2l. Portions a through 1 of FIGS. 3 and 4 correspond to the similarly denoted portions of FIG. 2.

Referring in more detail to FIG. 2, a sensor pulse is represented in FIG. 2a. When the sensor pulse crosses the threshold level determined by the source 82 of potential (FIG. 1) indicated on the ordinate in FIG. 2a, the output of the threshold amplifier 80 goes from a logic "one" to a logic "zero". This is denoted in FIG. 2b which is denoted amp. 80. As stated above, it is assumed that the duration of the sensor pulse is 30 microseconds, and the output of the amplifier 80 remains in the "zero" state for the 30 microseconds.

FIGS. 2c, d, and e, respectively denoted, multivibrator 87, NAND 86, and inverter 94 represent the outputs of those elements. The negative going transition at the input of the multivibrator 87 initiates the five microsecond change of state at the output of the multivibrator 87 (FIG. 2c). The NAND gate 86 will provide an output comprising a "zero" when both inputs thereto are "ones" and otherwise provide a logic "one" output. Consequently, the output of the NAND gate 86 assumes a "one" state for the longer of the "zero" outputs provided from the one shot multivibrator 87 or the width of the sensor pulse (above the threshold level). Thus, the first time period produced in response to a sensor pulse is defined. In the present case, the output of the NAND gate 86 changes state for 30 microseconds as shown in FIG. 2d. FIG. 2e representing the output of the inverter 94 is, of course, the binary complement of FIG. 2d. The end of the first time period is indicated by the transition of the output of the NAND gate 86 from a "one" state to a "zero" state.

This transition initiates a second time period. In the present embodiment, the second time period is initiated by the second one shot multivibrator 90 which is triggerable on negative-going transitions. As seen in FIG. 2f, denoted multivibrator 90, the output of the one shot multivibrator 90 changes state from "one" to "zero" for the duration of the present time for the one shot multivibrator 90, and the present embodiment, 5 microseconds. This output is provided to the inverter 105 which gates the analog switch 60 at its control terminal 64. The fixed time period of 5 microseconds is thus provided for incrementing the accumulation means 10 utilizing the level of potential and the output terminal 45. A precise time integral is thus provided to the accumulation means 10.

The output of the inverter 94 and one shot multivibrator 90 are utilized to maintain the analog switch 36 in the integrator 32 open during both the first and second time periods in the following manner. The signals represented in FIGS. 2e and 2f are supplied to the NAND gate 96 having its output represented in FIG. 2g denoted NAND 96. The first input to the NAND gate 96 is of a "zero" state during the first time period, and the second input thereto is in a "zero" state only during the second time period. Therefore, the NAND gate 96 assumes a "one" state for both the first and second time periods and otherwise assumes a "zero" state. Thus, the NAND gate 97 provides an output equal to the span of the first and second time periods. This output is followed by the buffer amplifier 102, as indicated in FIG. 2k denoted amp 102, for the 35 microsecond sum of the first and the second time periods. Consequently, as indicated in FIG. 2l, denoted Switch 36, the analog switch 36 is open during the first and second time periods to allow measurement of the sensor pulse (FIG. 2a), and for maintaining a level of potential at the terminal 45 for gating to the accumulation means 10 for a fixed span of time (FIG. 2f), and is otherwise closed. The basic operation is thus provided.

In order to make the timing and control circuit 6 responsive to a next pulse occurring while a given sensor pulse is being processed, the inverter 99, capacitor 98, and the source 100 operate as follows, (This operation will be discussed further with respect to FIG. 4). As seen in FIG. 2h, denoted inverter 99, the output of the inverter 99 comprises the binary complement of the second one shot multivibrator 90. The input to the NAND gate 97 is represented in FIG. 2i denoted capacitor 98. FIG. 2i represents the voltage across the capacitor 98 and consequently, the level of potential applied to the NAND gate 97. Until the end of a second time period, the potential source 100 maintains a logic level "one" input to the NAND gate 97. At the end of a second time period, the output of the second one shot multivibrator 90 returns to a high state (FIG. 2f). Consequently, the inverter 99 provides a negative-going transition, in the present embodiment to ground potential. Intuitively, this may be viewed as a negative "spike" which is AC coupled from the output of the inverter 99 to the input of the NAND gate 97. More rigorously stated, the capacitor 98 has one terminal dropped to ground potential and is recharged from the potential source 100. The values of the capacitor 98 and coupling resistor 101 are selected to provide, in effect, a logic "zero" output for one microsecond in response to the end of a second time period. This does not affect the normal operation described above.

Referring to FIG. 3, a sensor pulse having a duration of less than 5 microseconds is illustrated. In the present exemplification, a sensor pulse having a width of 3 microseconds beginning at time t0 is illustrated in FIG. 3a. Since the output of the amplifier 80 returns to the "one" state (FIG. 3b) before the end of the timer period initiated by triggering of the first one shot multivibrator 87 (FIG. 3c) the first time period ends at the end of the "zero" output from the first one shot multivibrator 87 (FIG. 3c). The second time period is initiated 5 microseconds after time t0 (FIG. 3f). The total of the first and second time periods is 10 microseconds, and is seen at the outputs of the NAND gate 97 and amplifier 102 (FIGS. 3j and 3k respectively). Operation proceeds as described with respect to FIG. 2.

FIG. 4 represents an example in which a first sensor pulse is initiated at time t0, ending at time t1 12 microseconds thereafter, and 3 microseconds after time t₂, at time t₃, a next sensor pulse having a span of 20 microseconds is initiated. Thus, the next sensor pulse occurs during processing of a first sensor pulse. Processing of the first sensor pulse beginning at time t0 proceeds in the same manner as described with respect to FIG. 2. However, at time t3 when the next sensor pulse is initiated, initial conditions are different. Comparing the conditions prior to time t3 in FIG. 4 and prior to time t0 in FIG. 2, it is seen that FIG. 4g, the output of the NAND gate 96 is already in a "one" state rather than a "zero" state; as seen in FIG. 4k, the switch 36 is open rather than closed. Thus the integrator 32 is already in a charged state, rather than being enabled to respond to the next sensor input pulse. As seen in FIG. 4i, at time t4, the "negative spike" is provided at the terminal of the capacitor 98 connected to the NAND gate 97. This logic "zero" signal is obtained in response to the ending of the second time period (FIGS. 4f and 4h) corresponding to the first sensor pulse. The resulting logic "zero" is NANDed with the output of the NAND gate 96 (FIG. 4g) at time t4. Consequently, the NAND gate 97 provides a one microsecond change of state, (FIG. 4j) beginning at time t4, which is coupled by the buffer amplifier 102 to open the switch 36 for 1 microsecond (FIGS. 4k and 4l respectively). Consequently, the integrator 32 is either completely reset or sufficiently discharged to permit the integrator 32 to generate a signal indicative of the second sensor pulse.

Summarizing, the methodology of the present invention is to sense the level of a sensor pulse provided at the input terminal 2 and generate a signal indicative of the level thereof. The generated signal is used for incrementing accumulation means, the accumulation means 10 in FIG. 1. Incrementing is performed by providing the potential level indicative of the size of a sensed cell to the accumulation means for a fixed period of time in response to the sensing of each cell. Provision of a first time period during which a sensor pulse exceeds the threshold level allows for providing an indication of the size of a cell indicated by a sensor pulse having more than one peak.

The foregoing has been written with a view toward enabling those skilled in the art to provide hematocrit measuring means constructed and operated in accordance with the present invention which may differ in detail from the specific embodiment illustrated.

What is claimed as new and desired to be secured by Letters Patent of the United States is:

1. Apparatus for measuring hematocrit comprising: peak detection means for connection to a sensor providing sensor pulses in response to blood cells in a sample, the sensor pulses each having a peak amplitude respectively corresponding to the size of a cell in response to which the sensor pulse is produced; storage means connected to said peak detecting means for generating and storing a signal having a level indicative of the peak value sensed by said peak detecting means for each pulse; accumulation means; controlled switching means coupling said storage means to said accumulation means, timing means responsive to said sensor pulses for initiating a first time period in response to each sensor pulse in excess of a threshold level and providing an output for enabling said storage means to respond to the sensor pulse, said timing means further including means for establishing a second time period in response to the completion of each first time period and providing an output for closing said controlled switching means for a fixed time period during said second time period, whereby said accumulation means is incremented by an amount in correspondence with the level of the stored signal in said storage means.

2. Hematocrit measuring apparatus according to claim 1, wherein said timing means further comprises means for establishing each said second time period at the end of each said first time period.

3. Hematocrit measuring apparatus according to claim 2 wherein said peak detector comprises a high impedance amplifier and said storage means is connected in a feedback amplifier, said timing means further comprises means for providing a reset signal to said storage means at the end of a second time period, said storage means comprises an analog integrator, said accumulation means comprises an analog integrator, and said means for coupling said storage means to said accumulation means comprises means for closing said controlled switching means for a fixed period of time during said second time period.

4. Hematocrit measuring apparatus according to claim 3 further comprising means for removing said resetting signal from said storage means in response to initiation of a next first time period following a first second time period.

5. Apparatus according to cliam 4 wherein said means establishing first time period comprises a threshold amplifier coupled to the sensor providing said sensor pulses, a one shot multivibrator connected for triggering by said threshold amplifier, and gating means connected to said threshold amplifier and said one shot multivibrator for providing a timing signal having a duration equal to the longer of the output of said one shot multivibrator or said threshold amplifier.

6. Hematocrit measuring apparatus according to claim 5 wherein said means for establishing said second time period comprises a second one shot multivibrator having said timing signal connected thereto for initiating said second time period on the expiration of said first time period.

7. Hematocrit measuring apparatus according to claim 6 wherein said controlled switching means comprises an analog switch having a control terminal coupled to the output of said second one shot multivibrator.

8. Hematocrit measuring apparatus according to claim 4 further comprising controlled switching means connected across said accumulation means and timing means for selectively maintaining said controlled switching means in an open state whereby accumulation means is enabled to accumulate a sum of the integrals of a plurality of stored signals from said storage means.

9. Hematocrit measuring apparatus according to claim 8 further comprising compensating input means for storing drift signals produced in said accumulation means and connected for common control by said timing means connected to said controlled switching means across said accumulation means.

10. Hematocrit measuring apparatus according to claim 7 further comprising scaling means connected to the output of said accumulation means for relating the output level of said accumulation means to a total volume of a sample whereby the output of said scaling means may be normalized in units of hematocrit percentage.

11. A method of measuring hematocrit comprising the steps of detecting the peak of each sensor pulse indicating a size of a blood cell in a sample passing through a sensor, establishing a first time period equal to at least the width of a sensor pulse, generating a signal indicative of the height of the sensor pulse within the first time period and storing the signal to provide a stored signal, establishing a second time period in response to the end of said first time period and incrementing accumulation means for a fixed time period by an amount in correspondence with said stored signal.

12. A method according to claim 11 wherein the step of establishing said first time period comprises establishing a said first time period equal to the longer of the width of the sensor pulse or a preselected time period.

13. A method according to claim 12 wherein the step of establishing said second time period comprises initiating said second time period at the end of said first time period.

14. The method according to claim 13 further comprising the step of normalizing the indication in said accumulation means to provide an output in units of hematocrit percentage.

* * * * *